United States Patent
Sun et al.

(10) Patent No.: US 9,119,692 B2
(45) Date of Patent: Sep. 1, 2015

(54) SHELL FORMS FOR MAKING PROVISIONAL AND LONG-TERM DENTAL RESTORATIONS

(71) Applicant: DENTSPLY International Inc., York, PA (US)

(72) Inventors: Benjamin Jiemin Sun, York, PA (US); Andrew M. Lichkus, York, PA (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 14/132,268

(22) Filed: Dec. 18, 2013

(65) Prior Publication Data
US 2014/0103557 A1    Apr. 17, 2014

Related U.S. Application Data

(63) Continuation of application No. 11/906,245, filed on Oct. 1, 2007, now Pat. No. 8,636,928.

(60) Provisional application No. 60/848,117, filed on Sep. 29, 2006.

(51) Int. Cl.
| | |
|---|---|
| *A61C 8/00* | (2006.01) |
| *A61C 5/10* | (2006.01) |
| *A61C 13/00* | (2006.01) |
| *A61C 13/20* | (2006.01) |
| *A61C 13/15* | (2006.01) |

(52) U.S. Cl.
CPC ............... *A61C 5/10* (2013.01); *A61C 13/0003* (2013.01); *A61C 13/20* (2013.01); *A61C 19/003* (2013.01); *Y10T 29/49567* (2015.01)

(58) Field of Classification Search
CPC ..................................... A61C 5/08; A61C 5/10
USPC ....................... 264/16, 19; 8/16, 19
See application file for complete search history.

(56) References Cited

U.S. PATENT DOCUMENTS

| | | | | |
|---|---|---|---|---|
| 4,695,705 | A | | 9/1987 | Kulig |
| 5,314,335 | A | * | 5/1994 | Fung ............................. 433/223 |
| 5,971,760 | A | * | 10/1999 | Letcher ......................... 433/223 |
| 6,010,337 | A | * | 1/2000 | Billet et al. .................... 433/218 |
| 6,884,073 | B2 | | 4/2005 | Chilibeck |
| 2004/0142305 | A1 | * | 7/2004 | Harlan .......................... 433/218 |
| 2004/0224283 | A1 | * | 11/2004 | Sun et al. ...................... 433/167 |
| 2011/0104641 | A1 | | 5/2011 | Sun et al. |

FOREIGN PATENT DOCUMENTS

| | | |
|---|---|---|
| WO | 9001727 A1 | 2/1990 |
| WO | 0110335 A1 | 2/2001 |
| WO | 2008042375 A1 | 4/2008 |

OTHER PUBLICATIONS

International Search Report, Application No. 2007/021165, Published Jan. 10, 2007.
International Written Opinion, Application No. 2007/021165, Published Jan. 10, 2007.

\* cited by examiner

*Primary Examiner* — Galen Hauth
(74) *Attorney, Agent, or Firm* — David A. Zdurne; Douglas J. Hura; Lena Levin

(57) ABSTRACT

The invention provides methods of making provisional and long-term dental restorations, particularly dental veneers, implants, crowns and bridges. A shell or restoration form made of polymerizable material having good dimensional shape-stability in its uncured condition is used to make the dental restoration. A polymerizable material is introduced into the cavity of the shell form. The outer shell and injected polymerizable material are polymerized and bond together to form a hardened crown structure. In one embodiment, the restoration can be fabricated indirectly by a dental laboratory. In another version, a dental practitioner can make the restoration chairside for a patient in a dental office.

20 Claims, No Drawings

SHELL FORMS FOR MAKING PROVISIONAL AND LONG-TERM DENTAL RESTORATIONS

CROSS-REFERENCE TO RELATED APPLICATIONS

This is a continuation application of U.S. Ser. No. 11/906,245, filed on Oct. 1, 2007, which claims the benefit of U.S. Provisional Patent Application 60/848,117 having a filing date of Sep. 29, 2006, the entire contents of which are hereby incorporated by reference.

BACKGROUND OF THE INVENTION

1. Field of the Invention

The present invention relates generally to methods and kits for making provisional and long-term dental crowns, bridges, inlays, onlays, veneers, implants, and other dental restorations. A shell or restoration form made of polymerizable material having good dimensional shape-stability is used to make the dental restoration. In one method, the restoration can be fabricated indirectly by a dental laboratory and sent to a dentist for placing in the mouth of a patient. In another version, the dentist can make the restoration in the dental office directly.

2. Brief Description of the Related Art

Dental restorations, such as crowns and bridges, are used to restore or replace lost tooth structure, teeth, or oral tissue. Provisional (or temporary) restorations are intended to be used for a relatively short time. For example, a dentist will often use a provisional crown, until a permanent crown is ready to be placed in the mouth of a patient. Following one conventional procedure, the dentist makes the provisional crown for the patient at the dental office and a dental laboratory makes the permanent crown. The dentist mounts the provisional crown to protect the tooth while the permanent crown is being made. Later, the dentist removes the provisional crown and replaces it with the permanent crown.

In one conventional method, the provisional crown is made using a prefabricated shell made of a metal such as aluminum, stainless steel, anodized gold, or polycarbonate. Because human teeth come in different sizes and shapes, many different shell forms must be available. The shell may be trimmed and shaped to fit properly over the prepared tooth structure. The shell cavity is typically filled with a polymerizable resinous material that may contain filler particulate. The shell containing the resinous material along with a temporary adhesive or cement is placed on the prepared tooth. The shell is irradiated with ultraviolet or visible light to cure the polymerizable resinous material and dental cement. Thus, the provisional crown is affixed to the tooth structure. Ideally, the shell form is shaped to achieve optimum margins, interproximal contacts, and occlusion. However, one problem with using prefabricated metal shell restorations is that they can be difficult to grind and shape. On the other hand, if polycarbonate shells are used, there can be problems with grinding the shell's occlusal surface—this may expose the filled resin and cause delamination and staining. Also, the bond strength between the shell and resin can be low even when a primer coating is used. Moreover, it is difficult to make adjustments to the rigid polycarbonate shell so as to obtain the desired bite surface. Another problem with using prefabricated metal shells is they may provide an esthetically non-pleasing appearance, and it can be difficult to find a shell that fits properly. One attempt to solve this problem involves providing many different shell forms having different sizes and shapes (for example, shells for molars and bicuspids). However, making so many different shell forms available to the dentist is expensive and time-consuming. As described further below, the polymerizable shell forms of this invention solve many of the problems associated with using conventional shell forms.

In recent years, techniques for making provisional crowns using prefabricated shells made of polymeric materials have been developed. For example, Rosellini, U.S. Pat. Nos. 5,192,207 and 5,332,390 disclose a method for making a permanent crown. After the tooth that will receive the crown has been prepared, a transparent shell tooth form is filled with a light-setting resin. The filled shell is placed on the prepared tooth and a light source (typically ultraviolet) is directed at thereon. This sets the light-setting resin and bonds the resin to the shell form. Preferably, the shell form is made from the same light-setting resin used to fill the shell so that there is good bonding therebetween. Thereafter, the tooth form is shaped and polished in situ to form the permanent crown.

Updyke, U.S. Pat. No. 5,775,913 discloses a method that allows a dentist to "cap" a tooth in a single office visit. The preferred material for making the crown shell or cap is known as ARTGLASS (Herarus Kulzer), a photopolymerizable multifunctional methacrylate monomer resin filled with different sized glass particles. The shell is prepared by molding and light-curing the ARTGLASS material. Then the cap is filled with an uncured, resinous material, preferably CHARISMA (Herarus Kulzer), a photopolymerizable multifunctional methacrylate monomer resin filled with glass particles. The cap is placed over the prepared tooth and the patient bites down. The dentist uses a curing light to cure the interior resin so that it bonds with the tooth and becomes integral with the cap.

Harlan, U.S. Pat. No. 6,935,862 discloses a method for making a crown, short-span bridge, or other dental prosthesis in a single office visit. The method involves placing a prefabricated shell that can be made from a polymerizable material, for example CRISTOBAL, a polyacrylic glass composite (Dentsply) over a prepared tooth. The shell is trimmed to achieve desired seating on the tooth and optimal occlusion. The shell is then removed from the tooth, and the tooth's prepared surface is painted with a separating medium. An interior surface of the shell is painted with a bonding agent, and an uncured composite material is added to the shell's cavity. Next the shell is positioned over the tooth, and the composite material in the cavity of the shell is partially light cured in situ. The shell is removed from the tooth and uncured composite material is added to the external surface of the shell. The added composite is then fully light cured, and the shell is affixed to the tooth.

Kvitrud et al., US Patent Application Publication US 2005/0042577 discloses dental crown forms having a handle attached to the crown form at a location removed from the base of the crown form. The crown form is filled with a hardenable material shortly before placing the crown form over the prepared tooth. The handle can be vented so that excess material can pass during placement of the crown form. One advantage with this crown form according to the published application is that the handle provides improved accessibility during placement of the crown form on the tooth. The published application notes that if the hardenable dental material is of a type that can retain its desired shape before hardening and after release from the interior surfaces of the dental crown form, the practitioner may remove the dental crown form before hardening the dental material.

In another instance, Chilibeck, U.S. Pat. No. 6,884,073 discloses a method for making temporary and semi-permanent crowns using a crown shell or form that is filled with resin. The crown form and resin are made from photopolymerizable materials, preferably comprising Bis-GMA. The crown form, having an incompletely polymerized layer is filled with resin. The crown is then fitted onto the tooth stub. The incompletely polymerized layer of the crown and injected resin are photopolymerized or autopolymerized in the mouth of the patient. The incompletely polymerized layer polymerizes with the resin as the resin is being polymerized.

As discussed above, there are numerous methods for making conventional provisional (temporary) dental restorations such as crowns and short-span bridges. A patient wears the provisional crown for a relatively short period of time, that is, until a permanent crown is made. Today, provisional crowns and bridges typically are used by a patient for a period of about three to six months. In general, such provisional restorations are effective, but there is a need in the dental field for restorations that can be used for longer periods. One object of the present invention is to provide dental restorations that can be used short-term (for example, a period of about one to twelve months) and long-term (for example, greater than twelve months).

The present invention provides methods for making such dental restorations using shell forms. A dental practitioner can use the resulting dental restoration as a provisional expecting that it will remain in the patient's mouth for a time period of about 1 to about 12 months. On the other hand, if the dental practitioner wishes to use the dental restoration as a long-term product, expecting that it will remain in the patient's mouth for a period of time longer than about 12 months, he or she can do so. The dental restorations of this invention can be used as either provisional or long-term dental products because of their advantageous properties. Particularly, the restorations are strong and durable and do not break or fracture easily. Because of their mechanical strength, the restorations can withstand hard occlusion forces. In addition, the restorations have pleasing aesthetics matching the shade of natural teeth. Moreover, the restorations have good margins and contacts, providing the patient with comfort while promoting dental health. The restoration covers and supports the tooth structure sufficiently so that it protects the tooth's pulpal portion.

Another object of the present invention is to provide a method that a dental laboratory can use to easily make dental crowns, bridges, inlays, onlays, veneers, implants, and other dental restorations having good mechanical strength, aesthetics, and occlusal fit.

Another object of this invention is to provide a method that a dental practitioner can easily use to design and fabricate the crown, bridge, or other dental restoration "chairside." This would help make the crown manufacturing and fitting process less time-consuming and costly. The dentist would be able to prepare and mount the crown on the patient's tooth in a single office visit. In such a method, the dentist should be able to check the crown and easily make adjustments, if needed, to achieve optimum comfort and fit. Another object of this invention is to provide a material which can be shaped and contoured easily to prepare a crown having good comfort and fit.

These and other objects, features, and advantages of this invention are evident from the following description and illustrated embodiments.

SUMMARY OF THE INVENTION

This invention provides methods for making provisional and long-term dental crowns, bridges, inlays, onlays, veneers, implants, and other dental restorations using polymerizable shell forms. In one version, a dental laboratory can make the restoration. This method involves providing a non-polymerized shell form comprising a polymerizable material. The shell form contains a cavity therein so that it can be mounted over a dental model of a patient's dental anatomy. A heated polymerizable material is introduced into the cavity of the shell form. The shell is then placed over an area of the dental model that will receive the restoration. The shell and polymerizable material are allowed to cool so as to form a dimensionally, shape-stable uncured restoration on the model. The shell and polymerizable material are irradiated with light so that the shell and polymerizable material cure and form a hardened restoration. The fully cured restoration is then removed from the model. The first and second polymerizable materials may comprise polymerizable acrylic compound and a polymerization system capable of being activated by light or heat for polymerizing the composition. Preferably, the polymerizable materials contain filler particulate. The first and second polymerizable materials may be the same or different compositions.

In another embodiment, a dental practitioner can make the dental restoration in the dental office. The restoration can be made while the patient is sitting in the dental chair. This method involves dispensing a heated polymerizable material into a non-polymerized shell form. The same polymerizable materials as described above can be used in this method. The practitioner positions the shell containing the polymerizable material in the mouth of a patient so the material is molded over the prepared tooth that will receive the restoration. Then, the shell and polymerizable material are irradiated with light to form a partially-cured restoration inside of the mouth. After removing the partially-cured restoration from the tooth, it can be irradiated with light outside of the mouth to form a fully cured restoration.

Another chairside method involves positioning the shell containing the polymerizable material in the mouth of a patient so the material is molded over the prepared tooth. The material is allowed to cool and harden to form a shape-stable restoration. The restoration remains shape-stable even though it is in an uncured condition. The shape-stable material can be partially-cured by a self (chemical) curing mechanism, thermal treatment, or irradiation with light. The partially-cured restoration can be removed and then irradiated with light to form a fully cured restoration.

DETAILED DESCRIPTION OF THE PREFERRED EMBODIMENTS

The present invention relates to methods of making dental crowns, bridges, inlays, onlays, veneers, implants, and other dental restorations using shell forms. In one embodiment, the restoration can be fabricated indirectly by a dental laboratory and sent to a dentist for placing in the mouth of a patient. In another version, the dentist can make the restoration at the patient's chair in the dental office.

The shell forms of the present invention are made from polymerizable dental material, which can either be an unfilled resinous composition or a filled resinous composition, that is, a composition containing filler particulate. The polymerizable material used in accordance with this invention comprises a polymerizable acrylic compound and polymerization initiation system, capable of being activated by light or heat, for polymerizing the material. Preferably, the polymerizable composition is a composite material containing filler particulate. By the term. "composite material" as used herein, it is meant that the material contains at least a portion of particulate filler. The polymerizable material and restorations prepared from such materials have certain properties, the test methods for measuring such properties being described below.

The polymerizable dental materials of the invention preferably include from about 0.1 to about 100 percent by weight of a crystalline resin and from about 0 to 100 percent by weight of an amorphous component. When heated, the polymerizable materials soften and are more flowable and have less crystallinity. The polymerizable materials can rapidly solidify. Rapid solidification provides the materials with a combination of flowable and dimensional stability properties, depending upon the temperature prior to polymerization. Furthermore, in a preferred embodiment, the polymerizable materials can partially recrystallize rapidly. This ability to rapidly recrystallize helps densify the polymeric products and provides the products with flowable and dimensionally-stable properties, depending upon temperature prior to polymerization. The polymerizable materials have several different characteristics, particularly that of: i) flowable dental composites at elevated temperatures, ii) of packable composites at lower temperatures as the material cools down; and iii) of wax-like composites at room temperature and body temperature. The polymerizable dental material includes a portion of crystals, which melt during polymerization. The crystalline portion is believed to include crystals of oligomer and/or crystals of monomer. The volume of the liquid formed by melting the crystals is greater than the volume of the crystals. This expansion reduces the shrinkage of the polymerizable dental material caused by polymerization.

"Crystallinity" as used herein refers to regularity and order within a material resulting in a heat of fusion of at least 1.0 J/g at and below 50° C. "Heat of Fusion" as used herein refers to enthalpy of fusion as determined by ASTM 793-95. Percent crystallinity is determined by measuring the heat of fusion using differential scanning calorimetry according to ASTM test method E 793-95.

"High strength dental polymeric material" as used herein means a material having flexural modulus of at least 200,000 psi and flexural strength of at least 5,000 psi. More preferably, the material has flexural modulus of at least 300,000 psi and flexural strength of at least 8,000 psi. Most preferably, the material has flexural modulus of at least 400,000 psi and flexural strength of at least 12,000 psi. The flexural strength and flexural modulus properties are measured according to ASTM D790 (1997).

"Wax-like" as used herein refers to material which is flowable (fluid) at and above 40° C., and becomes dimensionally stable (solidifies, that is, becomes non-fluid) at least at and below 23° C., within 5 minutes. Thus, wax-like material is flowable when it is at a temperature of 40° C. and greater, and becomes dimensionally stable when it is at a temperature of 23° C. and lower. Flowable wax-like material having a temperature from 100° C. to 40° C., becomes dimensionally stable within 5 minutes upon cooling by exposing it to ambient temperature between 37° C. and 0° C. Flowable wax-like composite paste having a temperature from 100° C. to 40° C., becomes dimensionally stable within (in order of increasing preference) 4, 2, 1 or 0.5 minutes upon cooling by exposing it to ambient temperature between 23° C. and 0° C.

"Dimensional stability" as used herein refers to material which is shape-stable as determined by testing methods according to ADA (American Dental Association) consistency test specification 19, Paragraph 4.3.4 (23° C.), JAVA Vol. 94, April, 1977, pages 734-737.

Polymerizable Materials
Polymerizable Acrylic Compounds

Polymerizable acrylic compounds that can be used in the composition of this invention, include, but are not limited to, mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexacrylate, 2,2-bis[4-(2-hydroxy-3-acryloyloxypropoxy)phenyl]propane; 2,2-bis[4-(2-hydroxy-3-methacryloyloxypropoxy)phenyl]
propane (Bis-GMA); modified Bis-GMA (the reaction product of Bis-GMA and 1,6 diisocyanatohexane); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), polyurethane dimethacrylate (PUDMA); 4,13-dioxo-3,14 dioxa-5,12-diazahexadecane-1,16-diol diacrylate; 4,13-dioxo-3,14 dioxa-5,12-diazahexadecane-1,16-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); alkoxylated pentaerythritol tetraacrylate; polycarbonate dimethacrylate (PCDMA); the bis-acrylates and bis-methacrylates of polyethylene glycols; and copolymerizable mixtures of acrylated monomers and acrylated oligomers.

In addition to the foregoing polymerizable acrylic compounds, the composition may contain acidic monomers such as dipentaerythritol pentacrylate phosphoric acid ester (PENTA); bis[2-(methacryloxyloxy)-ethyl]phosphate; and vinyl compounds such as styrene, diallyl phthalate, divinyl succinate, divinyl adipate and divinylphthalate. Diluent polymerizable monomers also may be added to the composition. For example, hydroxy alkyl methacrylates, ethylene glycol methacrylates, and dial methacrylates such as tri(ethylene glycol)dimethacrylate (TEGDMA) may be added to reduce viscosity and make the composition more suitable for application. A polymerizable acrylic compound can be used alone in the composition or mixtures of the compounds can be used. Mixtures of polymerizable monomers and oligomers, as described in the Examples below, are particularly preferred.

Polymerization System

A polymerization system can be used in the composition of this invention, which initiates polymerization (hardening) of the composition by a light-curable or heat-curable reaction. In one embodiment, a photoactive agent such as, for example, benzophenone, benzoin and their derivatives, or alpha-diketones and their derivatives is added to the composition in order to make it light-curable. A preferred photopolymerization initiator is camphorquinone (CQ). Photopolymerization can be initiated by irradiating the composition with blue, visible light preferably having a wavelength in the range of about 380 to about 500 nm. A standard dental blue light-curing unit can be used to irradiate the composition. The camphorquinone (CQ) compounds have a light absorbency maximum of between about 400 to about 500 nm and generate free radicals for polymerization when irradiated with light having a wavelength in this range. Photoinitiators selected from the class of acylphosphine oxides can also be used. These compounds include, for example, monoacyl phosphine oxide derivatives, bisacyl phosphine oxide derivatives, and triacyl phosphine oxide derivatives. For example, 2,4,6-trimethylbenzoyl-diphenyl-phosphine oxide (TPO) can be used as the photopolymerization initiator. In one embodiment, a material referred to as "ALF" comprising camphorquinone (CQ); butylated hydroxytoluene (BHT); N,N-dimethylaminoneopentyl acrylate, and methacrylic acid can be used in the composition.

In another embodiment, heat-activated polymerization initiators, such as peroxides, can be added to make the composition heat-curable. The peroxides generate free radicals to initiate polymerization and hardening of the composition at elevated temperature. Peroxides such as dibenzoyl peroxide (BPO), di-p-chlorobenzoyl peroxide, di-2,4-dichlorobenzoyl peroxide, tertiary butyl peroxybenzoate, methyl ethyl ketone peroxide, ditertiary butyl peroxide, dicumyl peroxide and cumene hydroperoxide, and the like can be used.

In addition to the photoactive and heat activated agents, the composition may include a polymerization inhibitor such as, for example, butylated hydroxytoluene (BHT); hydroquinone; hydroquinone monomethyl ether; benzoquinone; chloranil; phenol; butyl hydroxyanaline (BHT); tertiary butyl hydroquinone (TBHQ); tocopherol (Vitamin E); and the like. Preferably, butylated hydroxytoluene (BHT) is used as the polymerization inhibitor. The polymerization inhibitors act as scavengers to trap free radicals in the composition and to extend the composition's shelf life.

Fillers

Conventional filler materials, including reactive and non-reactive fillers, may be added to the composition. Reactive fillers include metal oxides and hydroxides, metal salts, and glasses that are acid-reactive. Such fillers are commonly used in dental ionomer cements. Examples of metal oxides include, but are not limited to, barium oxide, calcium oxide, magnesium oxide, and zinc oxide can be used. Examples of metal salts include, but are not limited to, aluminum acetate, aluminum chloride, calcium chloride, magnesium chloride, zinc chloride, aluminum nitrate, barium nitrate, calcium nitrate, magnesium nitrate, and strontium nitrate. Suitable glasses include, but are not limited to, borate glasses, phosphate glasses, and fluoroaluminate glasses. The glasses may or may not have fluoride-releasing properties. The benefits of using fluoride-releasing glasses are well known. Such materials are capable of releasing fluoride into the oral cavity over the long term. Fluoride generally provides added protection against acid attack that can cause tooth decay. Although, such fluoride-releasing glasses are generally not used in temporary dental restorations, since such restorations are intended for short-term use only. Organic particles such as poly(methyl methacrylate), poly(methyl/ethyl methacrylate), crosslinked polyacrylates, polyurethanes, polyethylene, polypropylene, polycarbonates and polyepoxides, and the like also can be used as fillers.

A wide variety of non-acid reactive filler materials and nanoparticles also can be added to the composition. Inorganic fillers, which can be naturally-occurring or synthetic, can be added. Such materials include, but are not limited to, silica, titanium dioxide, zirconia, alumina, iron oxides, silicon nitrides, glasses such as calcium, lead, lithium, cerium, tin, zirconium, strontium, barium, and aluminum-based glasses, borosilicate glasses, strontium borosilicate, barium silicate, lithium silicate, lithium alumina silicate, kaolin, quartz, and talc. Preferably, the silica is in the form of silanized fumed silica. A preferred glass filler is silanized barium boron aluminosilicate.

The average particle size of the particles comprising the filler material is normally in the range of about 0.1 to about 10 microns and more preferably in the range of about 0.1 to about 5 microns. If a fumed silica filler material is used, the silica particles are preferably nanometer-sized. Other nano-particles can be used in the composition if desired. The silica particles and nano-particles preferably have an average diameter of less than 200 nm. The filler particles can be surface-treated with a silane compound or other coupling agent to improve bonding between the particles and resin matrix. Suitable silane compounds include, but are not limited to, gamma-methacryloxypropyltrimethoxysilane, gamma-mercaptopropyltriethoxysilane, gamma-aminopropyltrimethoxysilane, and combinations thereof.

In one preferred embodiment, the composition comprises about 5 to about 15 wt. % TBDMA; about 3 to about 10 wt. % HDIDMA; about 1.5 to about 5 wt. % HDIDA; about 5 to about 10 wt. % UDMA; about 5 to about 10 wt. % EBPADMA; about 0 to about 0.5 wt. % TPO; about 0.1 to about 1.0 wt. % ALF and about 50 to about 80 wt. % filler material (silicon dioxide/glass). In another embodiment, the composition is substantially free of the ALF activator or TPO activator.

In yet another preferred embodiment, the composition comprises about 0 to about 10 wt. % TBDMA; about 3 to about 15 wt % modified Bis-GMA, about 2 to about 10 wt. % HDIDMA; about 0 to about 5 wt. % HDIDA; about 0 to about 10 wt. % UDMA; about 0 to about 10 wt. % EBPADMA; about 0 to about 0.5 wt. % TPO; about 0.1 to about 1.0 wt. % ALF and about 50 to about 80 wt. % filler material (silicon dioxide/glass).

These compositions were formulated to match the Refractive Index (RI) of the fillers used so as to obtain optimum translucency in the cured compositions. The matched RI of the components enabled the fabrication of translucent enamel layers of dental restorations and provided superior esthetics to the dental restorations.

TBDMA is added to the composition in the form of semi-solid high molecular weight oligomers. The addition of TBDMA provides the composite with good toughness and strength, good handling properties and adjusts the Refractive Index (RI) of the composite material to provide the desired translucency. HDIDMA and HDIDA are added as solid, semi-crystalline monomers. The $H_2O$ modified HDIDMA and HDIDA also provides a reduced crystallization time. Modified Bis-GMA, UDMA and EBPADMA are added as liquids in order to adjust filler load and softness at the uncured stage and increase the flowability of the composite material. These components also can further adjust the RI of the cured composite material, while assisting in decreasing the cure time. Lucirin-TPO and ALF are photoinitiators that initiate the polymerization of the monomers and oligomers and provide a relatively short cure time. Pigments are used to adjust the shade of the composite. The filler materials added to the composition to provide the composition with beneficial handling and mechanical properties.

As described further below, the composite material used in the method and shell forms of this invention is dimensionally stable when it is in its uncured state. The composite material, with its semi-crystalline components as described above, forms a hard, non-sticky surface layer upon being crystallized. The semi-crystalline components are partially recrystallizable and help the material to rapidly solidify. When polymerized, the crystallized phase melts effectively resulting in volume expansion, which offsets polymerization shrinkage somewhat. The resulting material has low shrinkage and stress.

The above-described composition can be used to manufacture shell forms, which can be used to fabricate dental crowns, bridges, inlays, onlays, veneers, and other dental restorations. Although the method of this invention is described primarily below as a method for making a dental crown, it should be understood that the method can be used to make any desired dental restoration.

Shell Forms

The shell forms used in the method of this invention can be made from the above-described polymerizable materials including polymerizable composite materials and unfilled resins. The color and shade of the prefabricated shell is carefully selected. For example, the shell can be made with a polymerizable material resembling the enamel layer and/or dentin layer of natural teeth. The enamel layer formulations generally have higher melting points and provide rigidity during manipulation while maintaining occlusal and enamel details. On the other hand, the dentin layer formulations generally have a relatively lower melting points that impart extended softness and working time. The shell forms can be made from, among other compositions, the enamel layer formulations, dentin layer formulations, or combinations thereof. Preferably, the shell form is made using a combination of the enamel and dentin layer formulations since they provide excellent esthetics and durability. The enamel and dentin layers offer superior esthetics with translucency and polychromatic color graduation of natural teeth. The combined layers provide fast and natural looking dental restorations. The polymerizable materials of this invention offer unique uncured shell forms with convenient handling, unique shape-stability, easy contouring at the uncured stage, improved strength and wear-resistance and superior esthetics. The polymerizable materials can be used by dental technicians and dentists to fabricate various restorations for provisional and long term applications.

The making of unique enamel shaded shell forms or multi-chromatic (both enamel and dentin shaded) shell forms enables the fabrication of multi-chromatic crowns and bridges with superb esthetics. In addition, the uncured shells, veneers, crowns, bridges, and implants of this invention offer unsurpassed advantages over conventional materials and methods for easy occlusal adjustment. Thus, restorations with ideal occlusal surfaces and comfortable bites can be made for the patient.

The polymerizable materials are quickly and easily reshaped, for example by warming; shaping the materials while warm; and then allowing the materials to cool to body (37° C.) or room temperature (23° C.). The cooled polymerizable materials may be worked, for example, by pressing, packing, molding, shaping, and/or carving. The worked polymerizable dental materials are then cured.

The melting point of the shell material is preferably about 0 to 50° C. higher than that of the dentin filling material of this invention. More preferably, the melting point of the shell material is about 1 to 30° C. higher and most preferably about 2 to 20° C. higher than that of the dentin filling material.

Methods

Indirect Dental Laboratory Method

In one method for making the dental crown, which can be referred to as an indirect dental laboratory method, the dentist prepares the tooth that will receive the crown by filing and grinding it to a "core" or "stump." A high-speed or low-speed handpiece equipped with a diamond bur is used to grind the tooth. The dentist takes a final impression of the patient's entire dental anatomy including the prepared tooth. Lastly, a conventional provisional crown can be mounted over the prepared tooth structure to protect it while the more permanent crown is being made in accordance with this invention.

The hardened impression is sent to a dental laboratory that will fabricate the crown. The dental technician, at the laboratory, prepares a cast (or model) by pouring dental plaster or stone into the hardened impression. This results in a finished plaster model having a shaped surface closely matching the patient's complete dental anatomy including the prepared tooth that will receive the crown. In other cases, the dentist will prepare the finished plaster models and send them directly to the laboratory.

The laboratory technician selects a prefabricated shell form made from the above-described polymerizable material. The color and shade of the prefabricated shell is carefully selected. The shell is then trimmed and adjusted so that it fits over a targeted area of the plaster model that will receive the crown. The shell form is in an uncured condition at this point so it can be trimmed, carved, stretched, molded or pressed easily to achieve a desired shape. The shell form is trimmed so that it can be tightly seated on the model and good margins, interproximal contacts, and occlusion can be achieved.

Next, the dental practitioner or laboratory technician dispenses a dental polymerizable material into the cavity of the shell form. The injected polymerizable material can be the same polymerizable material used to construct the shell, or the respective materials can be different as mentioned above. Preferably, a composite material containing filler particulate is used to fill the shell cavity. If different materials are used, they should still be compatible so they can cross-polymerize and bond with each other. The shell form containing the composite material is then seated and shaped over the area of the model requiring the crown. It is recognized that more than a single layer of the shaded composite material can be injected into the shell form. Preferably, the composite material is heated to a temperature generally above 40° C. and preferably to a temperature in the range of about 50° C. to about 100° C. If the temperature is too low, the material will not flow sufficiently. On the other hand, if the temperature is too high, the material will take a substantially long time to cool (solidify). Care should be taken that the correct amount of composite material is placed into the shell form. If a sufficient amount of composite material is not introduced, gaps will form in the resulting crown, and there will be occlusion problems. On the other hand, if too much composite material is introduced, the occlusion of the crown may be too high. This can occur even though the highly flowable nature of the heated composite material allows excess material to squeeze out easily. The shade of the composite material is carefully selected so that it matches the color of the patient's natural teeth.

Alternatively, in some cases, the shell form can be seated directly on the plaster model without first filling the shell form with composite material. The laboratory technician selects a shell form having the desired shade and shape. The shell form is in an uncured condition at this point so it can be trimmed, carved, stretched, molded or pressed easily to form an optimum crown structure. The technician can easily mold and shape the shell form over the area (prepared tooth) of the model requiring the crown.

In the case of making a short-span dental bridge, the technician may select shell form(s) to fit in edentulous areas on the dental model. The selected and prepared shell form(s) for pontic tooth (or teeth) in edentulous areas can be filled with selected shade composites or resins as prescribed by dentists so as to match the patient's natural dentition. The non-polymerized shell forms can be joined easily by melting the surface of the shell forms or adding selected shade composites or resins to join them together as needed.

The technician presses the filled pontic shell form on the surface of edentulous areas on the dental model to form the pontic. The filled material is allowed to harden. Then, the excess material is removed from the model. The resulting pontic(s) is ready to be joined with the crown form(s) using the composite material of this invention, which are polymerized together to form a hardened integral bridge. Alternatively, reinforcing metal, fiber, or ceramic bars or wires can be conveniently imbedded in the polymerizable material to enhance its strength and load bearing capability.

As discussed above, if the dentist has prepared the tooth for receiving the crown in the office visit and taken an impression of the prepared tooth, a dental model of the patient's dental anatomy including the crown-prepped tooth is fabricated. The dental laboratory may make this model, or the dentists may make this model at their office and send it to the laboratory. An oxygen barrier coating or other separating agent is applied to the surface of the model.

As described above, in the laboratory process for making a crown, once the shell form has been filled sufficiently with the composite material, it is placed over the area of the dental model that includes the tooth receiving the crown. Once seated, the shell form and composite material are allowed to set for approximately one to three minutes to form a shape-stable, uncured crown structure. Although the shell form and composite material are uncured at this point, they are dimensionally stable and remain substantially fixed in place. The shell forms and polymerizable materials have wax-like characteristics, good viscosity at elevated temperature, and favorable handling properties. The materials do not slump or substantially change shape. Contoured and molded to form a crown on the targeted area of the dental model, the shell forms and composite material do not expand or shrink substantially from that site.

If necessary, additional composite material or resin can be added to the external surface of the shell form to touch-up the crown as it is seated on the model. Any excess, composite material on the model also should be removed. The excess composite material can be removed from the model using a knife or other sharp instrument. Then, a thin layer of a visible light curing (VLC) sealer is applied to the surface of the crown. Now, the model, which is seated with the outer shell form and composite material in a crown shape, is placed in a light-curing oven and irradiated with curing light and heated in accordance with a pre-determined curing cycle. The curing time will depend upon many different factors including the light-curing oven used. In general, the materials of this invention completely set and harden in the range of about one (1) to about fifteen (15) minutes. The outer shell form and composite material are polymerized and bond together to form a hardened integral crown structure After the cured dental crown and supporting model are removed from the oven, the assembly is cooled. Then, the crown is removed from the model using fingers, a crown remover, or other suitable instrument. The crown is finished and polished using conventional techniques as needed. The crown can be polished using buffing wheels. Aluminum oxide can be used to steam-clean the interior surface of the dental crown for subsequent effective bonding to reline or cement material at the dentist's office. If needed, the crown also can be mechanically polished using buffing wheels and abrasives. Lastly, if the practitioner or technician wishes, a VLC sealant which provides a stain-resistant and glossy surface finish may be applied to the surface of the crown and the crown may be cured again in a light-curing oven.

The dental laboratory sends the finished crown back to the dentist. Once the dentist receives the crown, he or she can prepare the tooth that will receive the crown, if this has not already been done, by filing the tooth structure to a core or stump as described above. Then, the crown is affixed to the prepared tooth in the mouth of the patient using a suitable reline material and dental cement. Conventional dental cements, as are known in the dental field, may be used in this step. In cases where a temporary crown has been mounted over the tooth structure, it is first removed and then the crown of this invention is affixed to the tooth using dental cement.

In another embodiment, a substructure such as, for example, a metal coping can be used in the construction of the crown, bridge, or other restoration. The underlying substructure helps support the composite material used to make the restoration. Thus, the polymerizable composite material forms the visible portion of the crown and is bonded to the underlying substructure. Additional mechanical retention may be introduced to improve and maintain the integrity of bonding between the substructure and polymerizable composite material.

The strength and toughness of the crown can be enhanced by using a metal coping or other supporting substructure. Cast metals, alloys, ceramo-metal materials, high strength ceramics and fiber-reinforced composites can be used as copings or substructures for the restorations. The high strength ceramics include but not limited to alumina, zirconia, mullite, titanium oxide, magnesium oxide, SIALON and their mixtures. Metals and alloys and their mixtures, such as Nobel alloys, palladium-based alloys, cobalt-based alloys, nickel-based alloys, pure titanium and alloys, gold-based metal-ceramic alloys, nickel chromium alloys, etc. can be used as copings or substructures. Possible reinforcing fibers include glass, carbon, graphite, polyaramid, high density polyethylene, alumina, mixture thereof, as well as other fibers known in the art. It is understood that any suitable substructure can be used to make the crown, bridge, or other restoration in accordance with this invention. For example, ceramic (metal-free) substructures such as CERCON systems (Dentsply) and fiber-reinforced copings can be used as well as metal copings.

Dental Practitioner's Chairside Method

Following this method, a dental practitioner first prepares the patient's tooth that will receive the crown. Then the dental practitioner selects a shell form having the appropriate shade and shape for fitting over the prepared tooth in the patient's mouth. The shell form can be trimmed and adjusted as needed.

Next, the dental practitioner dispenses the dental composite material of this invention into the shell form and then immediately seats and shapes the shell over the prepared tooth. The composite material is heated. As discussed above, it is important that the correct amount of composite material be placed into the shell form. The shade of the composite material is also carefully selected and customized so that it matches the color of the patient's natural teeth. The dentist may wish to inject multiple layers of the shaded composite material into the shell form.

After filling the shell form with the composite material, the shell is inserted into the patient's mouth. It is positioned in the mouth in such a way that the composite material is molded and shaped over the prepared tooth that will receive the restoration. As the shell form is fitted in the mouth, excess composite material is allowed to escape around the margins and adjacent teeth. A single shell form is used to make the dental crown in this embodiment. Similarly, the dental practitioner can prepare bridges, inlays, onlays, veneers, implants, and other dental restorations. In cases where multiple shells are involved, the shells can be joined together by adding flowable composite, resin or adhesive, or by melting or adding the warmed polymerizable material. The shell forms are polymerized together to form a hardened integral bridge.

Alternatively, the dentist can prepare a model and work outside of the mouth. In this case, the dentist takes an impression of the prepared tooth (teeth) using conventional impression material. A model including a core or stump tooth structure is then made by pouring or injecting a low viscosity and suitably rigid die material, such as die silicone, plaster, dental stone, or the like into the hardened impression. Then, the shell form which contains the composite material as described above can be fitted over the dental model and a crown can be prepared. Following this method, the dentist can work extraorally to prepare the crown.

Moreover, in some cases, the shell form can be used directly on the prepared tooth in the patient's mouth without first filling the shell with composite material. The dental practitioner or laboratory technician selects a shell form having the desired shade and shape. The practitioner or technician can easily mold and shape the shell form over the area (prepared tooth) of the model requiring the crown. The shell form is in an uncured condition at this point so it can be trimmed, carved, stretched, molded or pressed easily to form an optimum crown structure in the patient's mouth. The shell form can be shaped and contoured so that it will have good margins, interproximal contacts, and occlusion.

Turning back to the chairside method described above, the shell containing the heated composite material is inserted into the patient's mouth and the material is allowed to cool and form a dimensionally stable, uncured crown structure. The uncured crown structure is then removed from the mouth. If needed, the dentist trims excess composite material away from the margins and adjacent teeth. Next, the uncured, shaped crown structure is placed back inside of the mouth so that the crown is positioned over the prepared tooth structure. The patient can bite down on the crown so that margins, contacts, and occlusion can be checked by the practitioner and adjusted accordingly. The fitted crown is then removed from the mouth.

Next, the crown is irradiated with light so that it cures and forms a fully hardened crown product. Preferably, the crown structure is first injected with a rapid self-curing silicone (die silicone or fast set plaster) to lock the crown shape in place and then it is placed in a light-curing unit. The injected die silicone or fast set plaster helps minimize potential shape distortion of the crown during the curing process. (The hardened die silicone or plaster is subsequently removed from the crown structure after the curing process.) Suitable light-curing ovens for curing the crown structure are available from Dentsply including, for example, the Eclipse® processing unit, Enterra® visible light-curing (VLC) unit, and Triad® 2000 VLC unit. Alternatively, a standard handheld dental curing light can be used. Suitable handheld Light units include halogen, plasma arc (PAC) and light-emitting diode (LED) dental curing lights include, for example, those sold under the brand names: QHL75® Lite (Dentsply), Spectrum® 800 curing unit (Dentsply), Optilux® 401 (Kerr), Sapphire (DenMat), SmartLite iQ2™ (Dentsply); Elipar® (3M Espe); and L.E. Demetron II™ (Kerr).

The crown can be finished with burs and polished using customary finishing techniques as needed. In addition, a VLC sealant, which provides a stain-resistant and glossy surface finish may be applied to the crown. The sealer helps provide the crown with improved esthetics and reduces polishing time.

The finished crown is now ready to be temporary or permanently affixed to the tooth. Conventional temporary or permanent cements, as known in the dental field, may be used in this step. In a second embodiment of this method, the composite material cools and forms a stable, uncured crown structure inside of the mouth. The shape-stable uncured crown structure remains in the mouth. The dentist can then trim excess composite material away from the margins of the crown and adjacent teeth. As the patient bites down on the crown, the margins, contacts, and occlusion can be checked by the practitioner and adjusted accordingly. Next, the shaped crown structure is partially cured in the mouth using a handheld dental curing light. Suitable curing lights for performing this partial curing step are described above. The partially cured crown is then removed from the mouth. It may be finished with a bur as needed. Optional, a die silicone may be injected into this partially cured crown to form a supporting model for optimal dimensional stability before final cure. In addition, a sealant, which provides a stain-resistant and glossy surface finish may be applied to the crown. A dental curing light or light-curing oven may be used to fully cure the crown structure.

A third version of this method is similar to the method described above, except there is no partial curing step. The composite material is completely cured outside of the mouth. Particularly, this method involves first cooling the composite material to form a stable, uncured crown structure within the mouth. The practitioner can check the crown fit and make any needed adjustments. Then, the shaped crown structure is removed, injected with die silicone to from a supporting model if desired and fully cure the structure by exposing it to light radiation outside of the mouth using dental curing lights or ovens.

Following a fourth method also is similar to the first method. First, the composite material is allowed to form a dimensionally stable, uncured crown structure and then it is removed from the mouth. After excess composite material is trimmed away from the margins and adjacent teeth, the uncured, shaped crown structure is placed back inside of the mouth so that the crown is positioned over the prepared tooth structure. The adjusted and fitted crown is then partially cured if the dentist wishes to perform this step. Then, the partially-cured crown can be removed and finished with burs and polished to its final desired shape. After applying a sealant to the crown's surface, it is ready to be fully cured and hardened. Optionally, a die silicone may be injected into this partially cured crown to form a supporting model.

In a fifth method, which is similar to the above-described third method, a self-cure composite or resinous material can be injected into the shell form and then immediately seated and shaped over the prepared tooth. Once the self-cure composite or resin has partially-polymerized, excess material is removed. Then, the partially-cured crown is removed from the prepared tooth so that the injected filling material can be additionally cured. The practitioner can then place the crown back onto the prepared tooth in the patient's mouth and check the crown fit and make any needed adjustments. Then, the shaped crown structure is removed, injected with die silicone to form a supporting model if desired, and fully-cured by exposing the structure to light radiation outside of the mouth using dental curing lights or ovens.

One advantageous property of the composite material and shell form used in this invention is that they can be shaped and molded to form stable, uncured crown structures. The molded, shape-stable crown can be partially light-cured inside of the mouth. This partial-curing step normally occurs after the margins, interproximal contacts, and occlusion have been checked and adjusted accordingly. The above-mentioned dental curing lights may be used to partially cure the material. Then, the partially-cured crown is removed from the mouth and finished with burs and polishers to its final desired shape. After applying a sealant to the crown's surface, it is ready to be fully cured and hardened. The crown may be placed in a standard light-curing oven, as mentioned above, and fully cured via light irradiation.

The uncured, shape-stable restorations prepared according to the methods of this invention have advantages over conventional materials with respect to occlusal adjustment, comfort, and fitting. For example, one problem with conventional materials occurs when the impression matrix or shell is seated over the prepared teeth. At this point, excess resin is forced into the gingival margins of the prepared tooth and it covers adjacent teeth and gum tissue. Upon curing, the excess resin forms a flash. This flashing must be removed and the cervical finish line of the restoration must be accurately adapted at the gingival margins to avoid initiating marginal gingivitis. Removing this cured flashing requires the use of finishing burs. It is very difficult to remove the cured flashing without damaging the cervical finish line or gingival tissue at the gingival margin. Furthermore, flashing below the gum line cannot be effectively removed without the risk of nicking or otherwise damaging adjacent teeth.

The disadvantages with conventional methods and restoration materials are overcome by the present invention. As discussed above, the dimensionally shape-stable uncured restorative can be molded, removed, carved or flowed as needed and excess flashing can be controlled. Furthermore, since the polymerizable materials and shell forms are shape-stable when they are in an uncured condition, even if excess material flow or flashing occurs, it can be removed easily without damaging the restoration.

The dental restorations produced by each of the methods of this invention have excellent properties and can be used as provisional or long-term restorations. Preferably, the restorations produced by this invention are high strength dental polymeric materials having a flexural modulus of at least 400,000 psi and a flexural strength of at least 5,000 psi. More preferably, the high strength dental polymeric materials have a flexural modulus of at least 1,000,000 psi and a flexural strength of at least 10,000 psi. In addition, the restorations can be custom-made so they accurately reproduce the polychromatic color graduation of natural teeth. A dental practitioner can use the dental restoration as a provisional expecting that it will remain in the patient's mouth for a time period of about 1 to about 12 months. Moreover, if there is a need, the dental practitioner can use the restoration long-term, expecting that it will remain in the patient's mouth for a period of time longer than about 12 months. The restorations have high mechanical strength, pleasing aesthetics, a hard and smooth surface finish, and good margins and contacts making them ideal products for protecting the dental health of a patient.

This invention meets the needs of the dental profession for quick and accurate ways to fabricate provisional and long-term crowns, bridges, and other restorations. Temporary, semi-permanent and permanent crowns, bridges and multi-tooth crowns, and other restorations can be fabricated conveniently in accordance with the methods of this invention. Several advantages are provided by these methods. For example, only a single shell form needs to be used, since it can be adjusted to fit several differently shaped teeth. The uncured shell forms are highly adjustable by pressing, molding, melting, and carving. The tooth colored dentin resins or composite materials can be dispensed easily to fill the shell form, once they are heated in conventional ovens, warm water baths, or by hot air guns, syringes or compule warmers, or other heating elements and methods. The finished restorations provide good fit and comfort without substantial drilling and trimming being required. In addition, the restorations are durable enough for provisional and long-term use.

The present invention is further illustrated by the following examples, but these examples should not be construed as limiting the scope of the invention.

Examples

In the following examples, unless otherwise indicated, all parts and percentages are by weight.

Example 1

Preparation of Oligomer

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes. To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

Example 2

Preparation of Monomer

A reaction flask was charged with 700 grams of 1,6-diisocyanatohexane and heated to about 70° C. under a positive nitrogen pressure. To this reactor were added 1027 grams of 2-hydroxyethyl methacrylate, 0.75 gram of catalyst dibutyltin dilaurate and 4.5 grams of butylated hydroxy toluene (BHT). The addition was slow and under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

Example 3

Preparation of Monomer

A reaction flask was charged with 168 grams of 1,6-diisocyanatohexane and heated to about 70° C. under a positive nitrogen pressure. To this reactor were added 228 grams of 2-hydroxyethyl acrylate, 0.12 gram of catalyst dibutyltin dilaurate and 0.86 grams of butylated hydroxy toluene (BHT). The addition was slow and under dry nitrogen flow over a period of two hours. The temperature of the reaction mixture was maintained between 70° C. and 85° C. for another three hours and followed by the addition of 0.9 grams of purified water. One hour later, the reaction product was discharged as clear liquid into plastic containers and cooled to form a white solid and stored in a dry atmosphere.

Example 4

Preparation of Monomer

A reaction flask was charged with 151.25 grams of octadecyl isocyanate and heated to about 70° C. under a positive nitrogen pressure. To this reactor were added 125.3 grams of caprolactone 2-(methacryloyloxy)ethyl ester, 0.12 gram of catalyst dibutyltin dilaurate and 0.58 grams of butylated hydroxy toluene (BHT). The addition was slow and under dry nitrogen flow over a period of two hours. The temperature of the reaction mixture was maintained between 70° C. and 85° C. for another 2.5 hours, the reaction product was discharged as clear liquid into plastic containers and cooled to form a semi-opaque solid and stored in a dry atmosphere.

Examples 5A and 5B

Tables 1 show the components of the compositions of Examples 5A and 5B. The compositions of Examples 5A and 5B were prepared by mixing the components shown in Table 1 at 85° C.

TABLE 1

Formulations of Wax-like Polymerizable Resins

| COMPONENTS | Example 5A (wt %) | Example 5B (wt %) |
|---|---|---|
| Titanium dioxide | 0.048 | 0.017 |
| Yellow Iron Oxide 7055 | 0.0021 | 0.0005 |
| Cromophtal Red-BRN 2-napthalenecarboxyamide, N,N'-(2-chloro-1,4-phenylene) bis{4-{(2,5-dichlorophenyl)azo}-3-hydroxy-} | 0.00087 | 0.0002 |
| Black Iron Oxide 7053 | 0.0026 | 0.0006 |
| Ultramarine Blue Pigment | | |
| A blend of 82.99% ZnO, 16.18% Magnesium carbonate, 0.62% Lithium sulfate and 0.21% Sulfur, (sublimed powder). [115 Phosphor] | 0.023 | 0.008 |
| Lumilux Blue LZ fluorescing agent (dihydroxy terepthalate acid ester) | 0.0096 | 0.0037 |
| Monomer of Example 4 | 0.8 | |
| Monomer of Example 3 | 20.98 | 6.85 |
| Monomer of Example 2 | 34.97 | 46.5 |
| Oligomer of Example 1 | 42.46 | 45.97 |
| 2,4,6- trimethylbenzoyl-diphenylphosphine oxide (Lucirin TPO) | 0.35 | |
| Camphorquinone | 0.047 | 0.087 |
| N,N-dimethyl-aminoneopentyl acrylate | 0.161 | 0.299 |
| Methacrylic Acid | 0.08 | 0.150 |
| Butylated Hydroxytoluene | 0.005 | 0.008 |
| γ-methacryloxypropylsilane | 0.057 | 0.106 |

Table 2 shows the physical properties of the selected compositions from Examples 5A and 5B, which have been polymerized by light cure in Triad light unit. The commercially available products, Integrity™, Triad® Provisional (sold by Dentsply International) and Jet acrylic (sold by Lang Dental) were prepared and cured according to manufacturing instructions.

TABLE 2

Physical Properties of Wax-like Polymerizable Resins and Commercially Available Provisional Materials

| Property/Characteristic | Example 5A | Example 5B | Jet Acrylics | Triad ® Provisional | Integrity ™ |
|---|---|---|---|---|---|
| Localized Wear (mm$^3$) | 0.027 | 0.04 | 0.19 | 0.087 | 0.174 |
| Flexural Modulus (MPa) | 3,580 | 3,550 | 2,260 | 2,870 | 2,900 |
| Flexural Strength (MPa) | 158 | 162 | 62.2 | 104 | 101 |

Volume loss (cubic mm at 400,000 cycles), was used as a measure of the wear-resistance of the polymerized compositions. A three body cyclic abrasion wear machine (Leinfelder method in vitro/University of Alabama) was used to determine volume loss. Samples were cured in a Triad® light curing unit for 10 minutes.

The enamel and dentin resin compositions cured by Triad® 2000 light unit showed good wear resistance, and improved properties over successful commercial products, Integrity™ Triad® Provisional, and Jet Acrylic.

Flexural Strength and Flexural Modulus of the polymerized compositions of this invention and the commercially available materials were measured by using three-point bend test on Instron bending unit according to ISO 10477. Polymerizable materials of this invention were cured in a Triad® light curing unit for 5 minutes for the Example 5A samples and 10 minutes for the Example 5B samples.

Example 6

Preparation of Monomer

A 200 mL reaction flask was charged with 14.0 grams of 1,12-diisocyanatododecane and heated to about 87° C. in a oil bath under a dry air pressure. To this flask were added 16.2 grams of 2-hydroxylpropyl methacrylate, 0.05 gram of catalyst dibutyltin dilaurate, and 0.11 grams of butylated hydroxy toluene (BHT). The addition was completed over a period of 34 minutes. The temperature of the reaction mixture was maintained around 90° C. for another 2.7 hours, the reaction product was discharged as a slightly cloudy liquid into a beaker and cooled to form a white solid and stored in a dry atmosphere. This monomer can be used to compound shape-stable polymerizable materials in accordance with this invention.

Example 7A

Crown Tooth Shell

Multiple crown tooth shells were formed by compressive molding a disk of the product of Example 5A in a two-part mold. The composition of Example 5A was preheated in a 60° C. oven before being compressed. Optionally, a thin elastic releasing film was used to enable the easy release from the molds, which may also be a part of the package.

Example 7B

Crown Tooth Shell

Multiple various crown tooth shells were prepared by pouring or injecting the melted product of Example 5B in two and three part molds, which formed shape stable shells upon cooling. The composition of Example 5B was melted and degassed in a 95° C. vacuum oven before being poured or injected.

Example 7C

Crown Tooth Shell

Multiple crown tooth shells were formed by stamping a disk of the product of Example 5D in a two-part mold. The composition of Example 5D was preheated in a 55° C. oven before being pressed. Optionally, a thin elastic releasing film was used to enable the easy release from the molds, which may also be a part of package.

Example 7D

Crown Tooth Shell

Multiple crown tooth shells were formed by compressive molding a piece of the product of Example 5A in a three-part mold. The composition of Example 5A was dispensed from a heated syringe before being compressed.

Example 7E

Crown Tooth Shell

Multiple various crown tooth shells were prepared by pouring or injecting the melted product of Example 5B in silicon mold cavities and then immediately placed in a matched silicone mold (part of this mold part was fitted inside the cavities of shells) to form shape stable shells upon cooling. The composition of Example 5B was melted and degassed in a 95° C. vacuum oven before being poured or injected. Optionally, the silicone mold(s) become(s) a part of the package.

Example 7F

Crown Tooth Shell

Multiple various two-layered crown tooth shells were prepared according to following steps. First, the melted product of Example 5B was poured or injected into silicon mold cavities and then immediately placed in a first matched silicone mold to form shape-stable enamel forms upon cooling. After the first matched silicone mold was removed from the silicone mold cavities to leave enamel forms remaining in the cavities, the melted product of Example 5A was poured or injected into silicon mold cavities and then immediately placed in a second matched silicone mold to form shape-stable shell forms upon cooling (part of this mold part was fitted inside the cavity of shell). This process formed shells with two layers of different shades. The compositions of Example 5A and 5B were melted and degassed in a 95° C. vacuum oven before being poured or injected. Optionally, the silicone mold(s) become(s) a part of the package.

Example 8

Tables 3 and 4 show the components of the compositions of Examples 8A through 8H. The compositions of Examples 8A through 8H were prepared by mixing and degassing the components shown in Tables 3 and 4 at 90° C.

TABLE 3

| | Formulations of Composite Resins | | | |
|---|---|---|---|---|
| Components | Example 8A (wt %) | Example 8B (wt %) | Example 8C (wt %) | Example 8D (wt %) |
| Oligomer of Example 1 | 8.072 | 8.033 | 8.072 | 8.033 |
| Monomer of Example 2 | 5.24 | 5.24 | 5.24 | 5.24 |
| Monomer of Example 3 | 3.50 | 3.50 | 3.50 | 3.50 |
| (HEMA-UDMA) Branched aliphatic urethane dimethacrylate (7,7,9-trimethyl-4,13-dioxo-3,14 dioxa-5,12-diazahexadecane-1,16-diol dimethacrylate) | 5.83 | 5.83 | 5.83 | 5.83 |
| Ethoxylated bisphenol A dimethacrylate* | 6.99 | 6.99 | 6.99 | 6.99 |

TABLE 3-continued

Formulations of Composite Resins

| Components | Example 8A (wt %) | Example 8B (wt %) | Example 8C (wt %) | Example 8D (wt %) |
|---|---|---|---|---|
| (Lucirin TPO)**** 2,4,6-Trimethylbenzoyldiphenyl phosphine oxide | | | 0.10 | 0.10 |
| Methacrylic acid | 0.085 | 0.085 | 0.06 | 0.06 |
| Butylated hydroxytoluene | 0.004 | 0.004 | 0.003 | 0.003 |
| N,N-dimethylaminoneopentyl acrylate | 0.163 | 0.163 | 0.117 | 0.117 |
| gamma-methacryloxypropyl trimethoxy silane | 0.050 | 0.050 | 0.036 | 0.036 |
| (Camphorquinone) bicyclo[2,2,1] heptane-2,3-dione-1,1,7-trimethyl-(IS) | 0.048 | 0.048 | 0.034 | 0.034 |
| Amorphous Silica (silaned) | 0.50 | | 0.50 | |
| Barium fluoro alumino borosilicate glass*** | 69.50 | 70.00 | 69.50 | 70.00 |
| Titanium Dioxide** | 0.017 | 0.050 | 0.017 | 0.050 |
| Yellow Iron Oxide 7055 | | 0.005 | | 0.005 |
| Cromophtal Red-BRN 2-napthalenecarboxamide, N,N'-(2-chloro-1,4-phenylene) bis{4-{(2,5-dichlorophenyl) azo}-3-hydroxy-} | | 0.0003 | | 0.0003 |
| Black Iron Oxide 7053 | | 0.001 | | 0.001 |
| Lumilux Blue LZ fluorescing agent (dihydroxy terepthalate acid ester) | 0.001 | 0.001 | 0.001 | 0.001 |
| Total % | 100 | 100 | 100 | 100 |

*SR348-purchased from Sartomer Company, Inc.
**Titanium Dioxide is one of three different types of TiO2: Titanox 328, 3328, 325
***Particles have one or more different average particle sizes and are selected from average particles sizes range from 0.1 micrometer to 10 micrometers.
****Lucirin TPO or TPO refers to 2,4,6-trimethylbenzoyldiphenylphosphine oxide made by BASF.

TABLE 4

Formulations of Composite Resins

| Components | Example 8E (wt %) | Example 8F (wt %) | Example 8G (wt %) | Example 8H (wt %) |
|---|---|---|---|---|
| Oligomer of Example 1 | 5.0926 | 4.0926 | 1.149 | 1.129 |
| Monomer of Example 2 | 4.00 | 5.25 | 4.00 | 4.54 |
| Monomer of Example 3 | 2.50 | 2.50 | 1.80 | 3.03 |
| (HEMA-UDMA) Branched aliphatic urethane dimethacrylate (7,7,9-trimethyl-4,13-dioxo-3,14 dioxa-5,12-diazahexadecane-1,16-diol dimethacrylate) | 5.00 | 5.00 | 5.00 | 5.05 |
| Ethoxylated bisphenol A dimethacrylate* | | 5.75 | 7.20 | |
| Modified Bis-GMA | 11.00 | 5.0 | 6.00 | 11.9 |
| (Lucirin TPO) 2,4,6-Trimethylbenzoyldiphenyl phosphine oxide | 0.10 | 0.02 | 0.02 | 0.10 |
| Methacrylic acid | 0.058 | 0.076 | 0.076 | 0.058 |
| Butylated hydroxytoluene | 0.003 | 0.004 | 0.004 | 0.003 |
| N,N-dimethylaminoneopentyl acrylate | 0.115 | 0.152 | 0.152 | 0.115 |
| gamma-methacryloxypropyl trimethoxy silane | 0.041 | 0.054 | 0.054 | 0.041 |
| (Camphorquinone) bicyclo[2,2,1] heptane-2,3-dione-1,1,7-trimethyl-(IS) | 0.033 | 0.044 | 0.044 | 0.033 |
| Amorphous Silica (silaned) | 0.50 | 0.50 | 0.50 | 0.50 |
| Barium fluoro alumino borosilicate glass*** | 71.50 | 71.50 | 74.00 | 73.50 |
| Titanium Dioxide** | 0.051 | 0.051 | | |
| Yellow Iron Oxide 7055 | 0.005 | 0.005 | | |
| Cromophtal Red-BRN 2-napthalenecarboxyamide, N,N'-(2-chloro-1,4-phenylene) bis{4-{(2,5-dichlorophenyl) azo}-3-hydroxy-} | 0.0001 | 0.0001 | | |
| Black Iron Oxide 7053 | | | | |

TABLE 4-continued

Formulations of Composite Resins

| Components | Example 8E (wt %) | Example 8F (wt %) | Example 8G (wt %) | Example 8H (wt %) |
| --- | --- | --- | --- | --- |
| Lumilux Blue LZ fluorescing agent (dihydroxy terepthalate acid ester) | 0.0013 | 0.0013 | 0.001 | 0.001 |
| Total % | 100 | 100 | 100 | 100 |

*SR348-purchased from Sartomer Company, Inc.
**Titanium Dioxide is one of three different types of TiO2: Titanox 328, 3328, 325
***Particles have one or more different average particle sizes and are selected from average particles sizes range from 0.1 micrometer to 10 micrometers.

TABLE 5

Mechanical Properties of Polymerizable Composites

| Compositions | Flexural Stress (MPa) | Flexural Modulus (GPa) | Wear Resistance-Volume Loss (mm$^3$) |
| --- | --- | --- | --- |
| 8A | 164 | 11.0 | 0.032 |
| 8B | 171 | 10.8 | 0.033 |
| 8C | 171 | 11.3 | 0.029 |
| 8D | 158 | 9.9 | 0.029 |
| 8E | 164 | 9.8 | 0.011 |
| 8F | 166 | 10.0 | 0.0133 |
| 8G | 153 | 10.0 | 0.0060 |
| 8H | 162 | 9.8 | 0.0145 |

Example 9A

Crown Tooth Shell

Multiple crown tooth shells were formed by compress molding a disk of the product of Example 8A in a two-part mold. The composition of Example 8A was preheated in a 60° C. oven before being compressed. Optionally, a thin elastic releasing film was used to enable the easy release from the molds, which may also be a part of the package.

Example 9B

Crown Tooth Shell

Multiple various crown tooth shells were prepared by pouring or injecting the melted product of Example 8C in two and three-part molds, which formed shape-stable shells upon cooling. The composition of Example 8C was heated to 70° C. before being poured or injected.

Example 9C

Crown Tooth Shell

Multiple crown tooth shells were formed by stamping a disk of the warmed product of Example 8A in a two-part mold. The composition of Example 8A was preheated in a 50° C. oven before being pressed. Optionally, a thin elastic releasing film was used to enable the easy release from the molds, which may also be a part of the package.

Example 9D

Crown Tooth Shell

Multiple crown tooth shells were formed by applying a thin layer of the heated product of Example 8C to form enamel layers in two or three-part mold. After the enamel layers were solidified, the heated product of Example 8D was added and compress molded in a three-part mold. The composition of Example 8D was dispensed from a heated syringe before being compressed. Multiple shells with two layers of different shades were made.

Example 9E

Crown Tooth Shell

Multiple various crown tooth shells were prepared by pouring or injecting the melted product of Example 8H, 8A or 8C in silicon mold cavities and then immediately placed in a matched silicone mold (part of this mold part was fitted inside the cavities of shells) to form shape-stable shells upon cooling. The compositions of Example 8H, 8A, or 8C were melted and degassed in a 85° C. vacuum oven before being poured or injected. Optionally, the silicone mold(s) become(s) a part of the package.

Example 9F

Crown Tooth Shell

Multiple various two-layered crown tooth shells were prepared according to following steps. First, the melted product of Example 8H, 8A, or 8C was poured or injected into silicon mold cavities and then immediately placed in a first matched silicone mold to form shape-stable enamel forms upon cooling. After the first matched silicone mold was removed from the silicone mold cavities to leave enamel forms remaining in the cavities, the melted product of Example 8E, 8B, or 8D was poured or injected into the silicon mold cavities and then immediately placed in a second matched silicone mold to form shape-stable shell forms upon cooling (part of this mold part was fitted inside the cavity of the shell). This process formed shells with two layers of different shades. The compositions of Example 8E, 8B, 8D, 8H, 8A, or 8C were melted and degassed in a 85° C. vacuum oven before being poured or injected. Optionally, the silicone mold(s) become(s) a part of package.

Example 9G

Crown Tooth Shell

Multiple various crown tooth shells were prepared by injecting the melted product of Example 8G in silicon coated mold cavities and then immediately placing it in a matched silicone coated mold (part of this mold part was fitted inside the cavities of the shells) to form shape-stable shells upon cooling. The composition of Example 8G was melted and degassed in a 85° C. vacuum oven before being injected into the mold cavities.

Example 9H

Crown Tooth Shell

Multiple various two layered crown tooth shells were prepared according to following steps. First, the melted product of Example 8G was injected into a two-part mold cavities and then immediately placed in a first matched silicone coated mold (part of this mold part was fitted inside the cavities of the enamel layers) to form shape-stable enamel forms upon cooling. After the first matched silicone coated mold was removed from the mold cavities to leave remaining enamel forms in the cavities, the melted product of Example 8F was injected into the mold cavities and then immediately placed in a second matched silicone coated mold. This formed shape-stable shell forms upon cooling (part of this mold part was fitted inside the cavities of the shells). This process formed shells with two layers of different shades. The compositions of Example 8F and 8G were melted and degassed in a 85° C. vacuum oven before being poured or injected.

Example 10

Chairside Crown Mounted Using Dental Cement

A dentist selected and prepared a suitable composite shell form made from Example 9B to match the shade and size of the tooth requiring the crown. After the tooth was prepped, the shell form was adjusted and the polymerizable composite of Example 8D was injected into shell form and seated on the prepped tooth to form a crown. After excess materials were removed, the uncured crown was occluded, contoured and adjusted easily (since it was shape-stable in the uncured state), and then removed from the tooth and trimmed. A fast set rigid silicone (optional) was injected into crown and sealer was applied. The crown structure was then cured in an Enterra™ light-curing unit (Dentsply) for 5 minutes to form a final crown, which was subsequently finished and polished. The finished crown was ready to be cemented on the crown-prepped tooth in the patient's mouth.

Example 11

Chairside Crown Mounted Using Dental Cement

A dentist selected and prepared a suitable composite shell form made from Example 9F of the polymerizable composite 8H to match the shade and size of the tooth requiring the crown. After the tooth was prepped, the shell form was adjusted and the polymerizable composite of Example 8E was injected into shell form and seated on the prepped tooth to form a crown. After excess materials were removed, this uncured crown was occluded, contoured, adjusted and cured with a handheld light for 5 seconds. It was then removed from the tooth and trimmed. A fast set rigid silicone (optional) was injected into the crown and sealer was applied. The crown structure was then cured in an Enterra™ light-curing unit (Dentsply) for 5 minutes to form a final crown, which was subsequently finished and polished. The finished crown was ready to be cemented on the crown-prepped tooth in the patient's mouth.

Example 12

Chairside Crown Mounted Using Dental Cement

A dentist selected and prepared a suitable composite shell form made from Example 9E to match the shade and size of the tooth requiring the crown. After the tooth was prepped and a thin layer of flexible spacer was applied and formed, TPH®3 Flow (Dentsply) was injected into the shell form and seated on the prepped tooth to form a crown. After excess materials were removed, this uncured crown was occluded, contoured, adjusted and cured using a handheld light for 5 seconds. The crown was then removed from the tooth and trimmed. A fast set rigid silicone (optional) was injected into the crown and sealer was applied. The crown structure was cured in a Triad® light-curing unit (Dentsply) for 10 minutes to form final crown. The crown was then removed from the light unit and shaped and contoured as needed. A thin layer of a visible light-curing sealer (optional) was applied to the surface of the crown and the crown was cured for about two minutes. The crown was subsequently finished and polished as needed. The finished crown was ready to be cemented on the crown-prepped tooth in the patient's mouth.

Example 13

Chairside Crown Mounted Using Dental Cement

A dentist selected and prepared a suitable shell form made from Example 7F to match the shade and size of the tooth requiring the crown. After the tooth was prepped, Integrity™ (Dentsply) was injected into the shell form and seated on the prepped tooth to form a crown. After excess materials were removed, the partially-cured crown was occluded, contoured, adjusted and then removed from the tooth and trimmed. (Alternatively, the partially-cured crown can be removed first and then placed back on the tooth to occlude, adjust and contour.) The crown structure is then removed from the mouth and trimmed. A fast set rigid silicone (optional) was injected into the crown and sealer was applied. The crown structure was cured in a Triad® light-curing unit (Dentsply) for 10 minutes to form a final crown. The crown was then removed from the light unit and shaped and contoured as needed. A thin layer of a visible light curing sealer (optional) was applied to the surface of the crown and the crown was cured for about two minutes. The crown was subsequently finished and polished as needed. The finished crown was ready to be cement on the crown-prepped tooth in the patient's mouth.

Example 14

Chairside Crown Mounted Using Dental Cement

A dentist selected and prepared a suitable composite shell form made from Example 9H to match the shade and size of the tooth requiring the crown. After the tooth was prepped, the shell form was trimmed, adjusted, seated, molded and pressed on the prepped tooth to form a crown. After excess materials were removed, this uncured crown was occluded, contoured, adjusted and light-cured using a handheld light for 5 seconds. The crown was then removed, trimmed, finished and polished. A fast set rigid silicone (optional) was injected into the crown and sealer was applied. The crown structure was cured in a Triad® light-curing unit (Dentsply) for 10 minutes to form a final crown, which was subsequently finished and polished. The finished crown was ready to be cemented on the crown-prepped tooth in the patient's mouth.

Example 15

Chairside Bridge Mounted Using Dental Cement

A dentist selected and prepared three suitable shell forms made from Example 7A to match the shade and size of teeth requiring the crowns and pontic (bridge). After the teeth were prepped, Integrity™ (Dentsply) was injected into shell forms and seated on the prepped teeth and pontic space to form multiple crown units. A flowable composite TPH®3 Flow was injected to join the shells together and the structure was tack-cured with a handheld light to form a bridge. After excess materials were removed, the partially-cured bridge was occluded, contoured, adjusted and then removed from the teeth and trimmed. (Alternatively, the partially-cured bridge can be removed first and then placed back on the teeth to occlude, adjust and contour). The bridge structure was then removed from the mouth and trimmed. A fast set rigid silicone (optional) was injected into the bridge and sealer was applied. The bridge structure was cured in an Enterra® light-curing unit (Dentsply) for 5 minutes and flip-cured for additional 1.5 minutes to form a final bridge. The bridge was then trimmed, shaped and contoured as needed. A thin layer of a visible light-curing sealer (optional) was applied to the surface of the bridge and the bridge was cured for about two minutes. The bridge was subsequently finished and polished as needed. The bridge was ready to be cemented on the crown-prepped teeth in the patient's mouth.

Example 16

Chairside Bridge Mounted Using Dental Cement

A dentist selected and prepared three suitable shell forms made from Example 9H to match the shade and size of the teeth requiring the crowns and pontic (bridge). After the teeth were prepped, the polymerizable composite material 8E was injected into shell forms and seated on the prepped teeth and pontic space to form multiple crown units. Heated composite 8E and heated tool were used to join the shells together and cool them to form the bridge. After excess materials were removed, this uncured bridge was occluded, contoured, adjusted and cured using a handheld light for 15 seconds. The partially-cured bridge was then removed from the mouth and trimmed and shaped. A fast set rigid silicone was injected into bridge and sealer was applied. The bridge structure was cured in an Enterra® light-curing unit (Dentsply) for 5 minutes and flip-cured for additional 1.5 minutes to form final bridge. The bridge was then trimmed, shaped and contoured as needed. The bridge was subsequently finished and polished as needed. The finished bridge was ready to be cemented on the crown-prepped teeth in the patient's mouth.

Example 17

Laboratory Fabricated Crown Mounted Using Dental Cement

First, a laboratory technician prepared the plaster model having a shaped surface closely matching the patient's complete dental anatomy including the tooth that was to receive the crown. Then, he selected and prepared a suitable shell form according to the dentist's recommendation to match the shade and size of the tooth requiring the crown. A shell form made from Example 7A was used. After the tooth for was prepped on the model, Jet Acrylic (Long Dental) was prepared and applied into the shell form and seated on the prepped tooth on the model to form a crown. After excess materials were removed, the crown was occluded, contoured and adjusted and then cured in a Triad® light-curing unit (Dentsply) for 10 minutes to form a final crown. Afterwards, a thin layer of a visible light-curing sealer (optional) was applied to the surface of the crown. The crown was then removed from the model and shaped and contoured as needed. An additional thin layer of a visible light curing sealer was applied to the surface of the crown and the crown was cured for about two minutes. The crown was subsequently finished and polished as needed. The laboratory fabricated crown was ready to send to the dentist to reline and cement on the crown-prepped tooth in the patient's mouth.

Example 18

Laboratory Fabricated Crown Mounted Using Dental Cement

First, a laboratory technician prepared the plaster model having a shaped surface closely matching the patient's complete dental anatomy including the prepared tooth that was to receive the crown. Then, he selected and prepared a suitable shell form according to the dentist's recommendation to match the shade and size of the prepared tooth. After a shell form made from Example 9H was selected, it was trimmed, seated and adjusted on the prepped tooth on the model. The heated polymerizable composite material of Example 8E was then injected into shell form and seated on the prepped tooth on the model. After excess materials were removed, this uncured crown was occluded, contoured and adjusted and then cured in a Triad® light-curing unit (Dentsply) for 10 minutes to form a final crown, which was subsequently finished and polished. A thin layer of a visible light-curing sealer (optional) was applied to the surface of the crown prior to curing or after curing (in case of applying sealer after cure, additional 2 minutes of curing time in the Triad® 2000 light-curing unit is needed). The crown was ready to be sent to the dentist to cement on the crown-prepped tooth in the patient's mouth.

Example 19

Laboratory Fabricated Bridge Mounted Using Dental Cement

First, a laboratory technician prepared the plaster model having a shaped surface closely matching the patient's complete dental anatomy including the teeth that was to receive the bridge. Then he selected and prepared suitable shell forms according to the dentist's recommendation to match the shade and size of the teeth requiring the bridge. Shell forms made from Example 9D were used. After the teeth were prepped on the model, the shell forms were trimmed, seated and adjusted on the prepped teeth on the model. The heated polymerizable composite material of Example 8D was injected into the shell forms and seated on the prepped teeth and pontic space to form multiple crown units. An electric spatula and additional composite of Example 8D were used to join shells together and cooled to form a bridge. After excess materials were removed, the bridge was occluded, contoured and adjusted easily since it was shape-stable and in the uncured state. A thin layer of a visible light curing sealer might be applied to the surface of the bridge, which was cured in an Enterra® light-curing unit (Dentsply) for 5 minutes and flip-cured for additional 1.5 minutes to form the final bridge. The bridge was then trimmed, shaped and contoured as needed. A thin layer of a visible light curing sealer (optional) was applied to the surface of this cured bridge and the bridge was cured for an additional two minutes. The bridge was subsequently finished and polished as needed. The bridge was ready to be sent to the dentist to reline and cement on the crown-prepped teeth in the patient's mouth.

Example 20

Laboratory Fabricated Bridge Mounted Using Dental Cement

First, a laboratory technician prepared the plaster model having a shaped surface closely matching the patient's complete dental anatomy including the prepared teeth that was to receive the bridge. Then, he selected and prepared suitable shells form according to the dentist's recommendation to match the shade and size of teeth requiring the bridge. Shell forms made from Example 9F were used, which were trimmed, seated and adjusted on the prepped teeth on the model. A ceramic reinforced bar was also prepared to reinforce the bridge. The heated polymerizable composite material of Example 8D was injected into the shell forms. The ceramic reinforced bar was imbedded in the shell forms and joined together using an electric spatula and seated on prepped teeth and pontic space to form multiple crown units. An electric spatula and additional composite material from Example 8D were used to completely join the shells together and cool them to form a bridge. After excess materials were removed, the bridge was occluded, contoured and adjusted. A thin layer of a visible light curing sealer might be applied to the surface of the bridge, which was cured in an Enterra® light-curing unit (Dentsply) for 5 minutes and flip-cured for an additional 1.5 minutes to form final bridge. The bridge was then trimmed, shaped and contoured as needed. A thin layer of a visible light curing sealer (optional) was applied to the surface of this cured bridge and the bridge was cured for an additional two minutes. The bridge was subsequently finished and polished as needed. The bridge was ready to send to the dentist to cement on the crown-prepped teeth in the patient's mouth.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method of making a dental restoration on a dental model of a patient's dental anatomy, comprising the steps of:
   a) providing a first polymerizable material;
   b) forming an uncured shape-stable shell from the first polymerizable material, the uncured shape-stable shell having a cavity therein;
   c) providing a second polymerizable material;
   d) forming an uncured shape-stable second form from the second polymerizable material, the uncured shape-stable second form having a cavity therein being complementary to the cavity of the uncured shape-stable first form;
   e) placing the second form in the first form to form an uncured shape-stable multi-layered shell, wherein the uncured multi-layered shell having a cavity therein is configured so that it may be mounted over the dental model;
   f) introducing a third polymerizable material into the cavity of the uncured multi-layered shell form;
   g) placing the uncured multi-layered shell form containing the third polymerizable material over a targeted area on the dental model that will receive the restoration;
   h) irradiating the uncured multi-layered shell and the third polymerizable material with light so they cure and form a hardened restoration; and
   i) removing the fully cured restoration from the model.

2. The method of claim 1, wherein the shell form is placed over the dental model prior to introducing the third polymerizable material into the cavity of the shell form.

3. The method of claim 2, wherein the shell form is trimmed and adjusted while it is positioned on the model.

4. The method of claim 1, wherein the first and second polymerizable materials each comprise a polymerizable acrylic compound and polymerization initiation system, capable of being activated by light or heat, for polymerizing the materials.

5. The method of claim 4, wherein the third polymerizable materials further comprise particulate filler.

6. The method of claim 4, wherein the first and second polymerizable materials have the same composition.

7. The method of claim 4, wherein the first and second polymerizable materials have different compositions.

8. The method of claim 4, wherein the polymerizable acrylic compound is a semi-crystalline material.

9. The method of claim 4, wherein the polymerization initiation system comprises a photoactive agent.

10. The method of claim 5, wherein the filler material is selected from the group of inorganic and organic materials and mixtures thereof.

11. The method of claim 1, wherein the uncured multi-layered shell form and third polymerizable material have shades resembling enamel shades of natural teeth.

12. The method of claim 1, wherein the uncured multi-layered shell form and third polymerizable material have shades resembling dentin shades of natural teeth.

13. The method of claim 1, wherein the uncured multi-layered shell form and third polymerizable material have shades resembling enamel and dentin shades of natural teeth.

14. The method of claim 1, wherein the restoration includes a supporting substructure.

15. The method of claim 14, wherein the substructure is a metallic material.

16. The method of claim 14, wherein the substructure is a ceramic material.

17. The method of claim 14, wherein the substructure is a fiber-reinforced composite.

18. The method of claim 1, wherein the uncured multi-layered shell is provided having an uncured enamel layer formed from the first polymerizable material and an uncured dentin layer formed from the second polymerizable material, the enamel layer having a higher melting point than the dentin layer.

19. The method of claim 1, wherein the first polymerizable material of the uncured multi-layered shell forms a first uncured enamel layer, the second polymerizable material of the uncured multi-layered shell forms a second uncured enamel layer, and the third polymerizable material introduced into the cavity of the uncured multi-layered shell forms an uncured dentin layer, the enamel layers having a higher melting point than the dentin layer.

20. The method of claim 1, wherein melting point of the first and second polymerizable materials are about 1 to 30° C. higher than the third polymerizable material.

* * * * *